(12) United States Patent
Mimura

(10) Patent No.: US 7,524,063 B2  
(45) Date of Patent: Apr. 28, 2009

(54) OPHTHALMIC APPARATUS

(75) Inventor: Yoshiaki Mimura, Gamagori (JP)

(73) Assignee: Nidek Co., Ltd. (JP)

( * ) Notice: Subject to any disclaimer, the term of this patent is extended or adjusted under 35 U.S.C. 154(b) by 574 days.

(21) Appl. No.: 10/722,052

(22) Filed: Nov. 26, 2003

(65) Prior Publication Data

US 2004/0114107 A1 Jun. 17, 2004

(30) Foreign Application Priority Data

Nov. 29, 2002 (JP) ............................. 2002-347237

(51) Int. Cl.  
*A61B 3/14* (2006.01)  
*A61B 3/10* (2006.01)

(52) U.S. Cl. .................. 351/208; 351/209; 351/204

(58) Field of Classification Search ................ 351/208, 351/206, 210, 211, 209, 221, 204  
See application file for complete search history.

(56) References Cited

U.S. PATENT DOCUMENTS

| | | | |
|---|---|---|---|
| 5,463,430 A | 10/1995 | Isogai et al. | |
| 5,644,375 A | 7/1997 | Suzuki | |
| 5,909,269 A * | 6/1999 | Isogai et al. | 351/208 |
| 6,135,596 A * | 10/2000 | Yoshida | 351/200 |

FOREIGN PATENT DOCUMENTS

| | | |
|---|---|---|
| JP | 06-304146 | 11/1994 |
| JP | 07-136119 | 5/1995 |
| JP | 08-173383 | 7/1996 |
| JP | 11-276436 | 10/1999 |
| JP | 2001-061782 | 3/2001 |
| JP | 2002-253506 | 9/2002 |
| JP | 2002-253513 | 9/2002 |

* cited by examiner

*Primary Examiner*—Ricky L Mack  
*Assistant Examiner*—Brandi N Thomas  
(74) *Attorney, Agent, or Firm*—Rader Fishman & Grauer PLLC (57) ABSTRACT

An ophthalmic apparatus capable of performing smooth examination. The apparatus includes a chin rest on which a chin of an examinee is placed, a chin rest moving unit which puts the chin rest into up/down movement, an examination unit which has an examination optical system for examining an eye of the examinee, a first moving unit which puts the examination unit into up/down movement with respect to the eye, an alignment condition detection unit which detects an alignment condition of the examination unit with respect to the eye, and a control unit which drives and controls the chin rest moving unit based on at least any one of a possible range of the up/down movement and a limit position of the up/down movement of the examination unit as well as a detection result obtained by the alignment condition detection unit.

4 Claims, 5 Drawing Sheets

OPHTHALMIC APPARATUS

BACKGROUND OF THE INVENTION

1. Field of the Invention

The present invention relates to an ophthalmic apparatus which examines an eye of an examinee.

2. Description of Related Art

In an ophthalmic apparatus for examining and measuring refractive power, intraocular pressure or the like of an eye of an examinee or for photographing and examining the eye, the eye is required to be in appropriate alignment with an examination unit having an examination optical system (a measurement optical system and/or a photographing optical system). Conventionally, when performing the alignment, a chin of the examinee is placed on a chin rest, and then an examiner manually moves the examination unit through operation of a joystick or the like while observing an image of an anterior-segment of the eye on a monitor. Alternatively, when the examiner has manually completed the alignment to some degree, the examination unit is automatically moved. On these occasions, the eye is sometimes positioned outside a possible range of up/down movement of the examination unit due to individual differences such as face size of the examinee. Therefore, in a conventional apparatus, when the examination unit is moved up/down to reach an upper limit/a lower limit, a limit display is presented on the monitor for informing the examiner of the necessity to move the chin rest up/down. And when the limit display is presented, the examiner manually moves the chin rest up/down.

However, the up/down movement of the chin rest after the presentation of the limit display is troublesome to the examiner and takes much examination time. Further, in a case where a self-examination apparatus is constituted such that the examination unit is moved through automatic alignment and the examinee him/herself conducts operation without the examiner, the alignment cannot be performed if the examination unit reaches its movement limit, thus stopping the examination.

SUMMARY OF THE INVENTION

An object of the invention is to overcome the problems described above and to provide an ophthalmic apparatus capable of performing smooth examination.

To achieve the objects and in accordance with the purpose of the present invention, an ophthalmic apparatus has a chin rest on which a chin of an examinee is placed, a chin rest moving unit which puts the chin rest into up/down movement, an examination unit which has an examination optical system for examining an eye of the examinee, a first moving unit which puts the examination unit into up/down movement with respect to the eye, an alignment condition detection unit which detects an alignment condition of the examination unit with respect to the eye, and a control unit which drives and controls the chin rest moving unit based on at least any one of a possible range of the up/down movement and a limit position of the up/down movement of the examination unit as well as a detection result obtained by the alignment condition detection unit.

Additional objects and advantages of the invention are set forth in the description which follows, are obvious from the description, or may be learned by practicing the invention.

The objects and advantages of the invention may be realized and attained by the ophthalmic apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
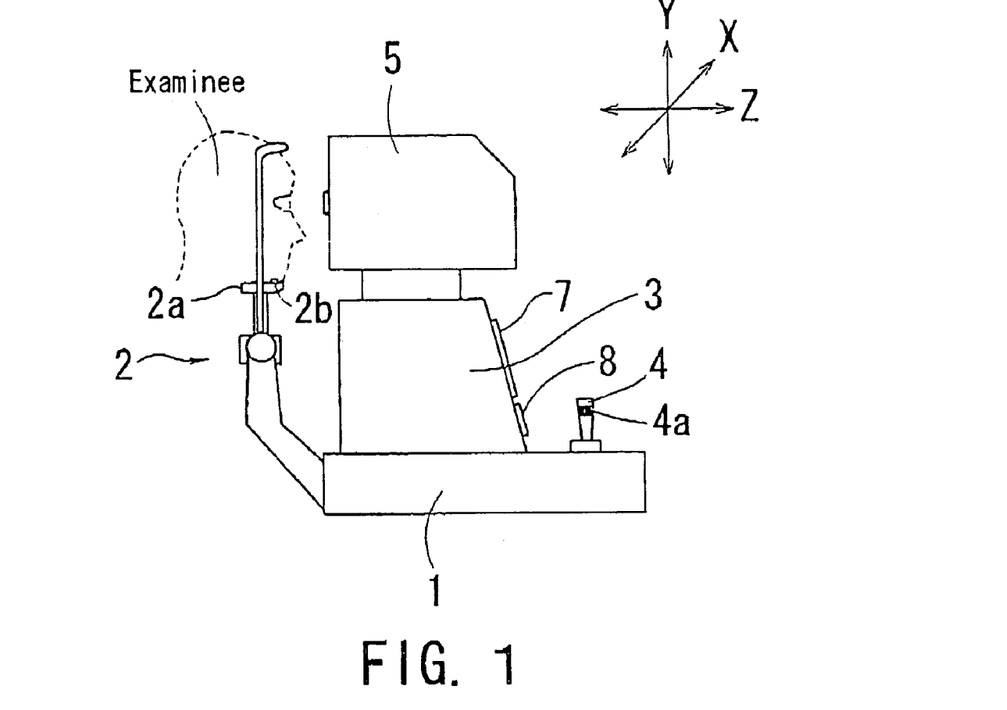
FIG. 1 is a side view showing a schematic configuration of an outer appearance of an ophthalmic apparatus consistent with the present invention.

A detailed description of one preferred embodiment of an ophthalmic apparatus embodied by the present invention is provided below with reference to the accompanying drawings. FIG. 1 is a side view showing a schematic configuration of an outer appearance of an ophthalmic apparatus consistent with the present invention.

Fixed to a base 1 of the ophthalmic apparatus is a face supporting unit 2 for supporting a face of an examinee. The face supporting unit 2 is provided with a chin rest 2a being movable up/down on which a chin of the examinee is placed. The chin rest 2a is moved up/down by a chin rest movement mechanism described later and is provided with a sensor 2b (a touch sensor or an optical sensor are also available) for detecting that the chin of the examinee is placed thereon.

Reference numeral 3 is a main body which is attached to the base 1, and reference numeral 5 is an examination unit 5 which stores an examination optical system and the like. The examination unit 5 is mounted on the main body 3 so as to be movable three-dimensionally in X, Y and Z directions with respect to an eye of the examinee by means of a Y-direction (up/down direction) movement mechanism 100 which is shown in FIG. 2, and an X-direction (right/left direction) movement mechanism 110 and a Z-direction (back/forth direction) movement mechanism 120 which are shown in FIG. 3, respectively.

Figure 2:
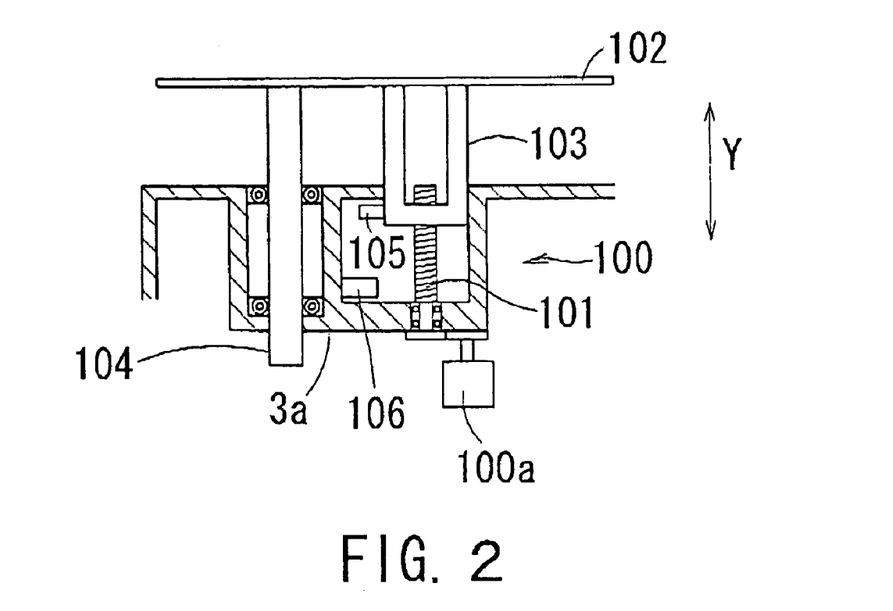
FIG. 2 is a view showing a Y-direction movement mechanism.

In FIG. 2, the Y-direction movement mechanism 100 has a constitution that a feed screw 101 is rotated via a gear by a pulse motor 100a fixed to the main body 3, so that a female screw portion 103 fixed to a Y table 102 is moved up/down to put the Y table 102 into up/down movement. A guide shaft 104 is fixed to the Y table 102 and is moved up/down along a bearing attached to a frame 3a of the main body 3. A shielding plate 105 is attached to the female screw portion 103, and a photosensor 106 for sensing the shielding plate 105 is provided on the flame 3a of the main body 3. The photosensor 106 senses the shielding plate 105 as sensing that the Y table 102 has been moved down to reach a lower limit.

Figure 3:
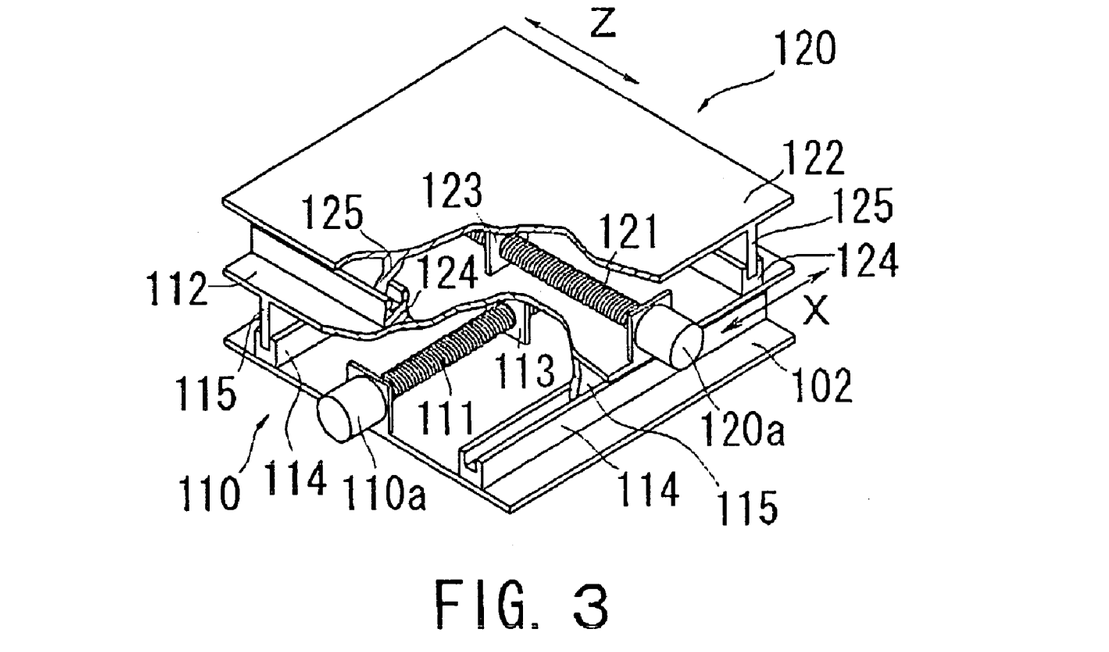
FIG. 3 is a view showing X- and Z-direction movement mechanisms.

In FIG. 3, the X-direction movement mechanism 110 has a constitution that a feed screw 111 is rotated via a gear by a pulse motor 110a fixed to the Y table 102, so that a female screw portion 113 fixed to an X table 112 is moved right/left to put the X table 112 into right/left movement. Guide grooves 114 are fixed to the Y table 102, and guide shafts 115 are fixed to the X table 112. As in the case of the X-direction movement mechanism 110, the Z-direction movement mechanism 120 has a constitution that a feed screw 121 is rotated via a gear by a pulse motor 120a, so that a female screw portion 123 fixed to a Z table 122 is moved back/forth to put the Z table 122 into back/forth movement. Guide grooves 124 are fixed to the X table 112, and guide shafts 125 are fixed to the Z table 122.

In FIG. 1, a joystick 4 is used in a case where the examiner performs alignment. The joystick 4 is tilted back/forth and right/left so that the examination unit 5 is moved in the Z and X directions (back/forth and right/left directions). In addition, a rotation knob 4a of the joystick 4 is rotated and controlled to move the examination unit 5 in the Y direction (up/down direction). On the examiner's side of the main body 3, a monitor 7 and a switch unit 8 including a mode-selecting switch and the like are provided.

Figure 4:
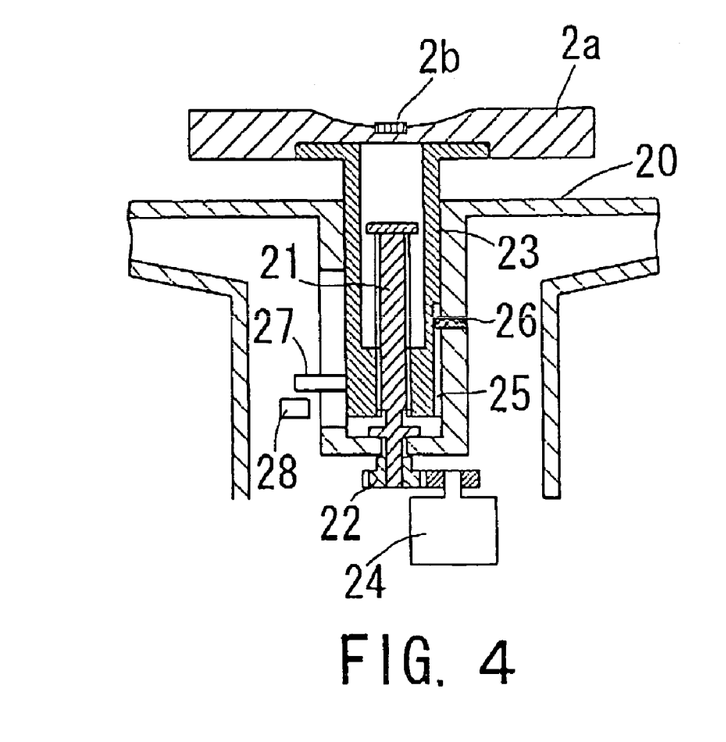
FIG. 4 is a view showing an up/down movement mechanism of a chin rest.

FIG. 4 is a view showing an up/down movement mechanism of the chin rest 2a. A feed screw 21 is provided upright in a supporting base 20, and a pole 23, having a female screw portion which is in helical engagement with the feed screw 21, is attached movable up/down as guided by the supporting base 20. The chin rest 2a is fixed on the pole 23. Provided in the lower part of the feed screw 21 is a gear 22, with which a gear attached to the pulse motor 24 is engaged. In addition, the pole 23 has a groove 25, and the groove 25 and a screw 26 for stopping rotation prevent the pole 23 from rotating. The feed screw 21 is rotated as the motor 24 is rotated, so that the chin rest 2a is moved up/down in conjunction with the pole 23. A shielding plate 27 is attached to the lower part of the pole 23, and a photosensor 28 which senses the shielding plate 27 is provided on the supporting base 20. The photosensor 28 senses the shielding plate 27 as sensing that the chin rest 2a has been moved down to reach a lower limit.

Figure 5:
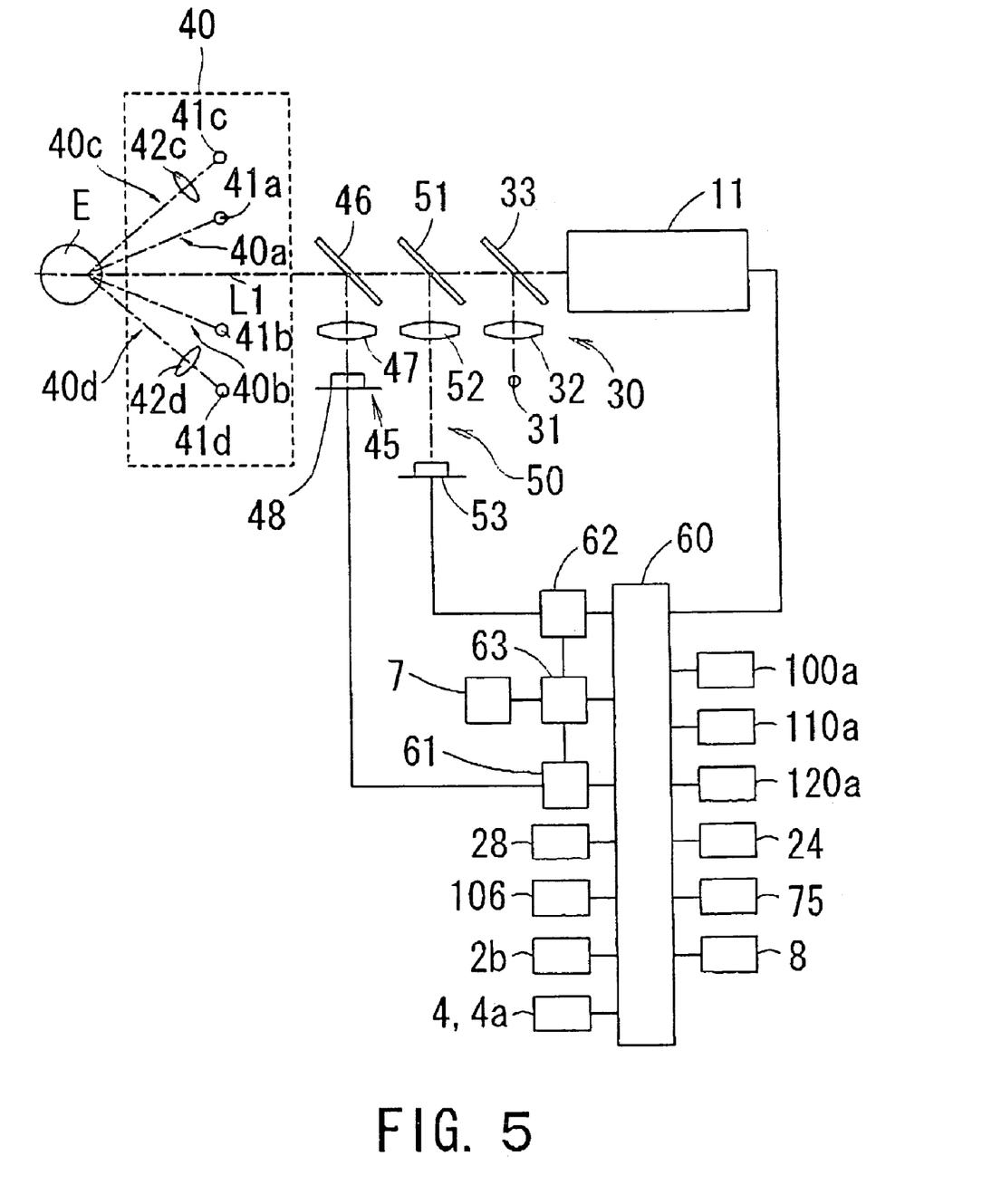
FIG. 5 is a view showing a schematic configuration of an optical system and a control system in the present apparatus.

FIG. 5 is a view showing a schematic configuration of an optical system and a control system in the present apparatus. An examination optical system 11 is arranged inside the examination unit 5 and has an optical axis L1. The examination optical system 11 is for example an eye refractive power measurement optical system. Since a known constitution may be adopted to the eye refractive power measurement optical system, its details are omitted.

Further, an alignment target projection optical system and an alignment condition detection optical system are arranged inside the examination unit 5. The alignment target projection optical system consists of a first target projection optical system 30 and a second target projection optical system 40.

The first target projection optical system 30 projects an alignment target for detecting the alignment condition in the X and Y directions (right/left and up/down directions) from the front of the eye E of the examinee. A target (infrared light) from a infrared point light source 31 is made approximately collimate (parallel) by a lens 32, and goes via half mirrors (or dichroic mirrors) 33, 51 and 46 arranged on the optical axis L1 to be projected onto the eye E.

The second target projection optical system 40 projects alignment targets for detecting the alignment condition in the Z direction (back/forth direction) from a slanting direction of the eye E, and is provided with two projection optical systems 40a and 40b which are arranged symmetrically about the optical axis L1 and of which optical axes form a predetermined angle, and two projection optical systems 40c and 40d which are arranged symmetrically about the optical axis L1 and of which optical axes form a greater angle than the projection optical systems 40a and 40b. The projection optical systems 40a and 40b, which consists of infrared point light sources 41a and 41b, project targets (infrared light) at a finite distance on to the eye E. The projection optical systems 40c and 40d, which consists of infrared point light sources 41c, 41d and collimating lenses 42c, 42d, project targets (infrared light) at an infinite distance onto the eye E. Besides, the projection optical systems 40a to 40d are arranged so as to project the targets on a single meridian in a horizontal direction with respect to the eye E.

The alignment condition detection optical system is provided with a first detection optical system 45 and a second detection optical system 50. The first detection optical system 45 is provided with the half mirror 46, a lens 47, and a CCD camera 48 having sensitivity to a visible range which picks up an image of a face region including both eyes of the examinee under low magnification. The second detection optical system 50 is provided with the half mirror 51, a lens 52, and a CCD camera 53 having sensitivity to an infrared range which picks up an image of the eye E under high magnification, and detects images of the alignment targets projected onto the eye E from the alignment target projection optical system. Incidentally, the eye E of which image is picked up by the second detection optical system 50 is illuminated by an infrared light source not illustrated, and the face region of the examinee of which image is picked up by the first detection optical system 45 is illuminated by a visible light source not illustrated.

Hereinafter, the constitution of the control system will be described. The CCD camera 48 is connected with a first image processing unit 61 which performs processing for obtaining detection information about a positional relationship of the eye E with the optical axis L1 being an examination optical axis. The CCD camera 53 is connected with a second image processing unit 62 which performs processing for obtaining detection information about a positional relationship in the X, Y and Z directions with respect to the eye E from the detected images of the alignment targets. Output signals from the first image processing unit 61 and the second image processing unit 62 are respectively inputted to a control unit 60. The control unit 60 is connected with pulse motors 100a, 110a and 120a for moving the examination unit 5 in the X, Y and Z directions, respectively.

In addition, the control unit 60 is connected with the photosensors 106 and 28. During the initial stages of the operation, the control unit 60 moves the examination unit 5 and the chin rest 2a down. After the photosensors 106 and 28 sense that the examination unit 5 and the chin rest 2a reach the lower limits, respectively, the control unit 60 drives and controls the pulse motors 100a and 24 assuming that the examination unit 5 and the chin rest 2a are in original positions. A reference position of the movement in the Y direction of the examination unit 5 is the approximate center of the possible range of up/down movement. A reference position of the movement of the chin rest 2a is at a predetermined distance above the lower limit. Each travel position (distance) is controlled by the number of driving pulses for each motor with reference to the original positions sensed by the photosensors 106 and 28. Likewise, sensing mechanisms are provided which senses original positions in the X and Z directions of the examination unit 5, respectively. The examination unit 5 is moved to the original positions during the initial stages of the operation, and then the predetermined number of pulses is given to the pulse motors 110a and 120a to move the examination unit 5 to the reference positions in the X and Y directions. A reference position of the movement in the X direction is the approximate center of a possible range of right/left movement, and a reference position of the movement in the Z direction is the farthest position from the eye E.

A display control unit 63 controls information to be displayed on the monitor 7. Further, the control unit 60 is connected with a voice generation unit 75 which emits a voice guide for guiding the examinee.

The operation of the ophthalmic apparatus provided with the above-mentioned constitution will be described. The apparatus is furnished with a first examination mode in which the examinee him/herself conducts the examination through automatic alignment and a second examination mode in which the examiner conducts the examination along with alignment operation. Either mode is previously selected by using the mode-selecting switch of the switch unit 8. Firstly, a case in the first examination mode will be described.

Figure 6:
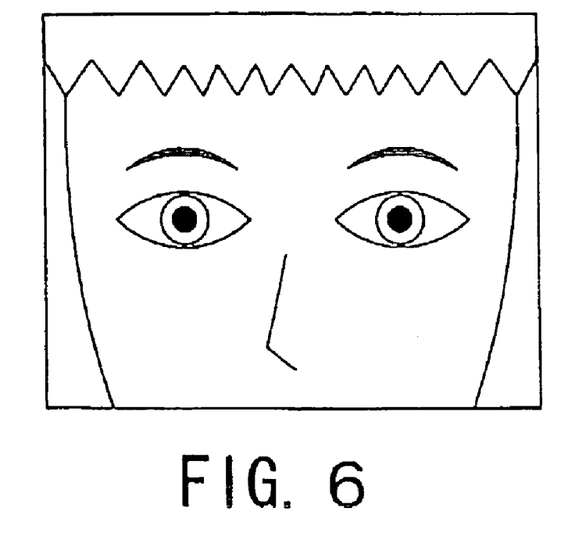
FIG. 6 is a view showing an image of a face region including both eyes of an examinee picked up by a detection system under low magnification.

When the chin of the examinee is placed on the chin rest 2a, a detection signal from the sensor 2b is inputted to the control unit 60. The control unit 60 starts the automatic alignment taking the detection signal from the sensor 2b as a trigger. To begin with, positions of both eyes of the examinee are detected based on the image under low magnification picked up by the CCD camera 48 (see FIG. 6). The first image processing unit 61 performs edge extraction on the image obtained by the CCD camera 48. The face has characteristics that many edges exist in eyes. Therefore, data on the image including edges is analyzed for the horizontal and vertical directions, respectively, and distribution of the edges thus obtained may be used to nearly specify the eye positions. (Even if the edges appear greatly also in brows, a shape thereof in the horizontal and vertical directions respectively may be observed to enable differentiation.) When the eye positions are nearly specified, light and shade information is derived from the image thereabout, and a black portion in the pupil is extracted. Since the pupil is the most black part about the eye, the eye position in the X and Y directions may be specified.

The control unit 60 moves the examination unit 5 with respect to the eye which is firstly examined (for example, the right eye) based on the detection information about the eye positions. The control unit 60 obtains a deviation amount D of the eye with respect to the reference position in the Y direction of the examination unit 5 from the image picked up by the CCD camera 48. When the deviation amount D is greater than the possible range of up/down movement of the examination unit 5, the motor 24 is driven to move the chin rest 2a up/down.

Figure 8A:
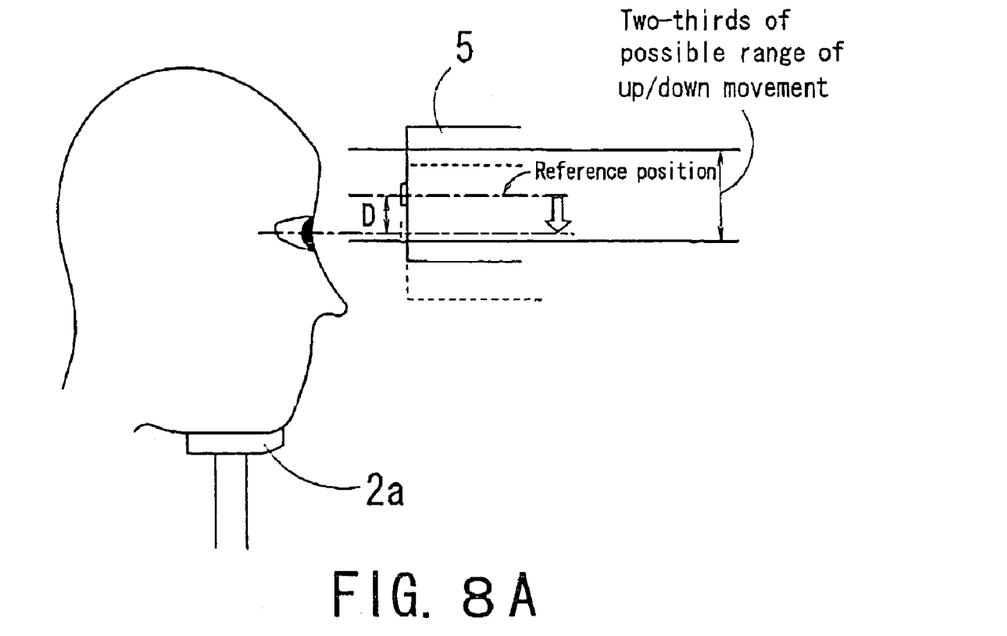
FIGS. 8A and 8B are views showing operation of the chin rest and an examination unit when a chin of the examinee is placed on the chin rest.
Figure 8B:
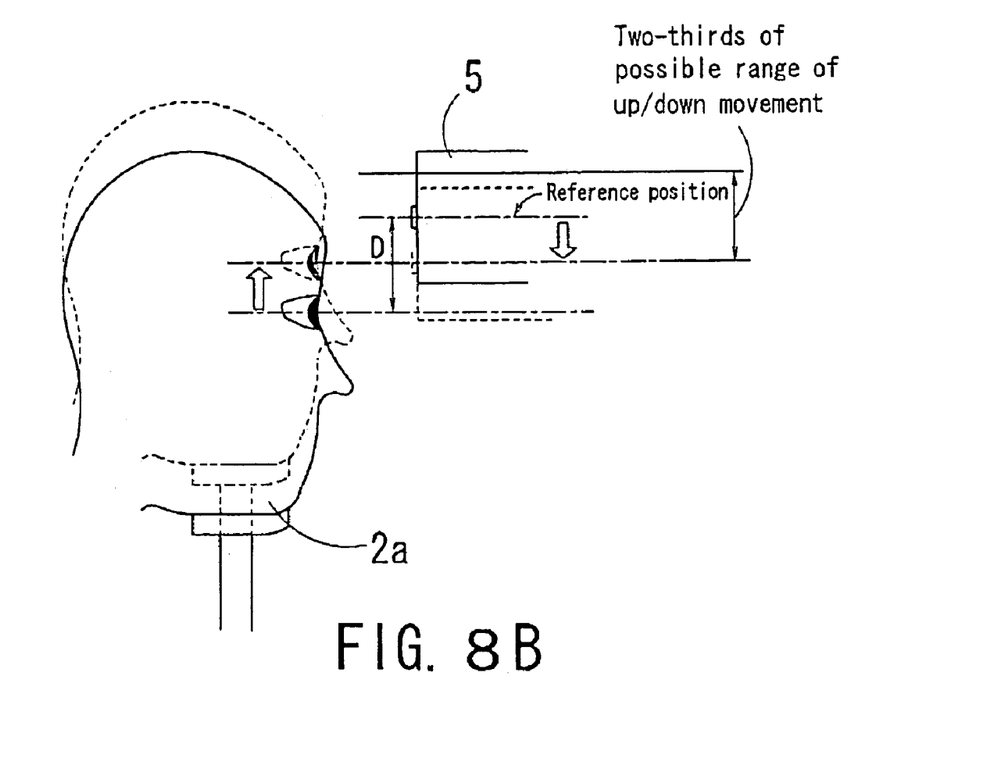

A method for judging whether or not to move the chin rest 2a based on the deviation amount in the Y direction will be described with reference to FIGS. 8A and 8B. As criteria for judgment, the chin rest 2a is not moved in a case where the deviation amount D of the eye with respect to the reference position in the Y direction of the examination unit 5 (a center position of the possible range of up/down movement) is within two-thirds of the possible range of up/down movement of the examination unit 5 (for example, 13 mm or smaller on one side when the possible range of up/down movement is 40 mm). The criteria for judgment whether or not to move the chin rest 2a is set within a narrower range than the possible range of up/down movement of the examination unit 5 because one-third of the possible range of up/down movement (7 mm on one side) for the examination unit 5 is left so that the automatic alignment and automatic tracking may be fully conducted with respect to the eye by moving only the examination unit 5. For example, as shown in FIG. 8A, in a case where the eye is placed below the reference position in the Y direction of the examination unit 5, and the deviation amount D of the eye is within two-thirds of the possible range of up/down movement, only the examination unit 5 is moved down assuming that the automatic alignment and the automatic tracking are fully achievable by moving the examination unit 5. Incidentally, the movement position in the Y direction with respect to the reference position in the Y direction of the examination unit 5 is obtained from the number of driving pulses for the motor 100a. The deviation amount D of the eye with respect to the reference position in the Y direction of the examination unit 5 is obtained from a relative position of the eye to the optical axis of the examination unit 5 and the travel position of the examination unit 5.

On the other hand, in a case where the deviation amount D is beyond two-thirds of the possible range of up/down movement, the chin rest 2a is moved to fall within two-thirds of the possible range of up/down movement. For example, as shown in FIG. 8B, when the eye is positioned below the reference position in the Y direction of the examination unit 5 and is outside two-thirds of the possible range of up/down movement, the motor 24 is driven to move the chin rest 2a up so that the eye is positioned above the lower limit of two-thirds of the possible range of up/down movement. At this time, the examination unit 5 is simultaneously moved from the reference position in the Y direction to the lower limit of two-thirds of the possible range of up/down movement. The alignment may thereby be performed speedily. When the examination unit 5 comes to satisfy requirements for the automatic alignment and the automatic tracking, the alignment may be completed thereafter by moving only the examination unit 5.

Figure 7:
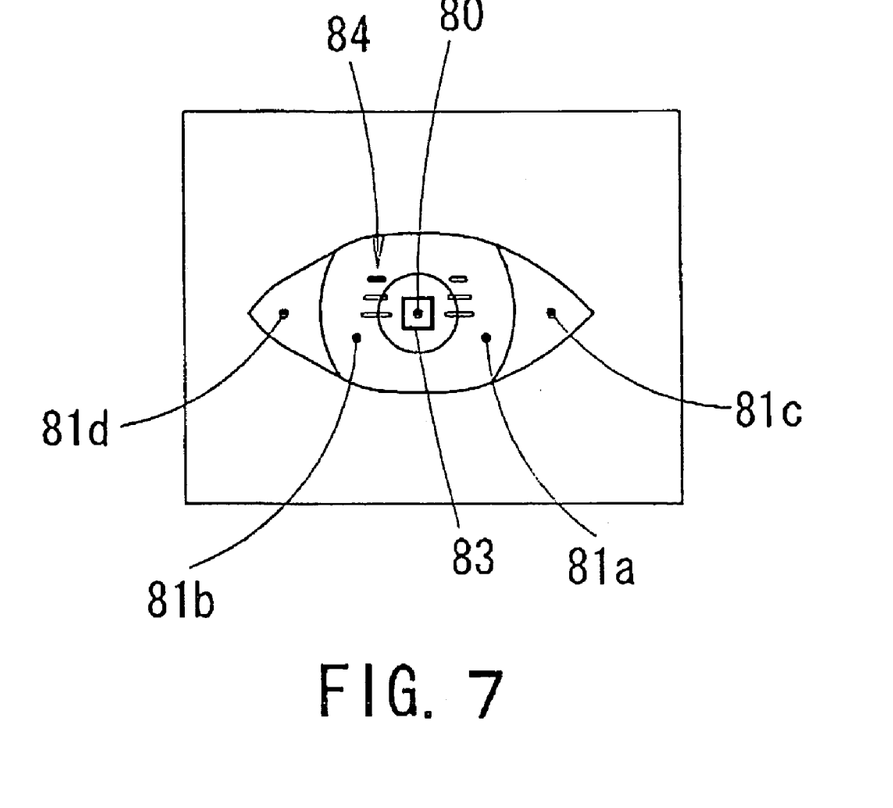
FIG. 7 is a view showing an image of an anterior-segment of an eye of the examinee picked up by a detection system under high magnification.

When the eye and the examination unit 5 are in rough alignment and the alignment target images become detectable by the CCD camera 53, the movement of the examination unit 5 is converted to control based on the detection of the alignment target images. The target images detected by the CCD camera 53 are detected and processed by the second image processing unit 62. FIG. 7 shows an image of an anterior-segment of the eye picked up by the CCD camera 53. The control unit 60 obtains deviation in the X and Y directions from a target image 80 positioned at the center, which is projected from the first target projection optical system 30, and drives and controls the Y-direction movement mechanism 100 and the X-direction movement mechanism 110 to move the examination unit 5. In addition, the alignment condition in the Z direction is detected by comparing intervals between infinite target images 81c, 81d and finite target images 81a, 81b (see Japanese Patent Application Unexamined Publication No. Hei 6-46999 corresponding to U.S. Pat. No. 5,463, 430 for details). Based on detection results, the control unit 60 drives and controls the Z-direction movement mechanism 120 to move the examination unit 5 in the Z direction. When the alignment condition in the X, Y and Z directions are judged to be appropriate, the control unit 60 automatically emits a trigger signal to implement the examination by the examination optical system 11.

Incidentally, the alignment detection mentioned above utilizes the image under low magnification picked up by the CCD camera 48. However, if the eye is in such a range that the CCD camera 53 may pick up the image of the eye, the eye may be detected by using only the CCD camera 53. In a case where only the CCD camera 53 is used to detect the eye position, as for the alignment in the X direction, the reference position of the examination unit 5 is previously moved right to a position at a half distance of an averaged distance between pupils from the center of the movement range of the examination unit 5. By doing this, the right eye of the examinee easily falls in the image-pickup range of the CCD camera 53, and the alignment may be immediately started.

Further, as for the alignment in the Y direction, the chin rest 2a may be moved after the movement limits in the up/down direction are detected by the movement of the examination unit 5. In this case, it is preferable that the chin rest 2a is moved to fall within a narrower range than the movement range with the upper or lower limit of the examination unit 5. For example, when the examination unit 5 reaches the lower limit, as mentioned above, the chin rest 2a is moved up so that the eye is positioned not only above the lower limit but also within two-thirds of the possible range of up/down movement. Thereby, the automatic alignment (including the automatic tracking) may be completed by moving the examination unit 5 without moving the chin rest 2a thereafter. Besides, a relative distance between the eye and the optical axis L1 of the examination unit 5 is calculated from alignment detection results obtained by the CCD camera 48 or 53. The number of driving pulses for the photosensor 106 and the pulse motor 100a exhibits detection that the examination unit 5 has reached the upper or lower movement limit (or the distance to the movement limits).

When moving the chin rest 2a, the control unit 60 informs the examinee of the movement by the voice guide from the voice generation unit 75 and then drives the motor 24 to move the chin rest 2a. Thereby, the alignment may be performed with examinee's understanding while not surprising the examinee.

After the completion of the right-eye measurement, the control unit 60 moves the examination unit 5 in the X direction for converting to the left-eye measurement. At this time, if the examination unit 5 is moved based on the detection results on the distance between the pupils obtained from the image picked up by the CCD camera 48 (or the averaged distance between the pupils), the alignment detection may be performed based on the target images on the anterior-segment picked up by the CCD camera 53. When the target images cannot be detected, the image picked up by the CCD camera 48 may be used. As for the alignment of the left eye in the Y direction, the alignment of the right eye has been set within two-thirds of the possible range of up/down movement of the examination unit 5, so that the alignment of the left eye may be completed by moving only the examination unit 5.

After the completion of the examination for both eyes, a printer not illustrated outputs examination results, and the examination unit 5 is returned to the reference position in the X, Y and Z directions as a preparation to a next examinee. The chin rest 2a is also returned at the reference position (height).

Next, a case in the second examination mode will be described. The chin of the examinee is placed on the chin rest 2a to support the face of the examinee. The examiner observes the image of the anterior-segment displayed on the monitor 7 (or the image under low magnification picked up by the CCD camera 48) and controls the joystick 4 and the rotation knob 4a to move the examination unit 5 in the X, Y and Z directions, respectively. An operation signal from the joystick 4 and the rotation knob 4a is inputted to the control unit 60, and the control unit 60 drives each motor in accordance with the operation signal.

Incidentally, for example, when the movement of the examination unit 5 down to the movement limit is sensed by the photosensor 106 and the number of driving pulses for the motor 100a, the control unit 60 drives the motor 24 to move the chin rest 2a up based on the alignment detection results from the image picked up by the CCD camera 48 or 53 so that the eye is positioned within two-thirds of the possible range of up/down movement. Alternatively, as in the case of the aforementioned first examination mode, the chin rest 2a may be moved up at the point when the eye is judged to be positioned below the movement limit of the examination unit 5. When the chin rest 2a is moved and the image of the anterior-segment becomes observable on the monitor 7 as shown in FIG. 7, the examination unit 5 is moved in the X and Y directions so that the target image 80 is positioned at the center of a reticle 83 displayed on the monitor 7. Further, the alignment in the Z direction is performed in accordance with the display of an indicator 84. As mentioned above, the alignment condition in the Z direction is judged based on the detection results of the target images 81a to 81d given by the second target projection optical system 40. When a positional relationship between the target image 80 and the reticle 83 as well as the indicator 84 are in a predetermined state, the examiner depresses an examination starting switch not illustrated to perform eye refractive power measurement. Incidentally, the operation up to the rough alignment may be performed by the examinee, and the automatic alignment may be implemented based on the alignment detection results after the target image 80 and the like become detectable.

As described above, according to the present invention, smooth examination may be performed without causing trouble to the examiner or the examinee.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:
   a base;
   a face supporting unit which is fixed to the base;
   a chin rest being movable up/down with respect to the face supporting unit, on which a chin of an examinee is placed;
   a first moving unit having a motor, which puts the chin rest into up/down movement;
   an examination unit being movable up/down with respect to the base, which has an examination optical system for examining an eye of the examinee;
   a second moving unit having a motor, which performs alignment of the examination unit with respect to the eye of the examinee fixed to the face supporting unit by putting the examination unit into up/down movement;
   an image pickup unit which picks up an image of the eye of the examinee fixed to the face supporting unit; and
   a control unit which
   obtains a deviation amount of the eye in an up/down direction from a reference position of the examination unit in the up/down direction based on the image picked up by the image pickup unit,
   judges whether or not the obtained deviation amount is outside a predetermined possible range of the alignment in the up/down direction, which is narrower than a possible range of the up/down movement of the examination unit by the second moving unit, performs the alignment of the examination unit with respect to the eye by driving the motor of the second moving unit if the obtained deviation amount is not outside the predetermined possible range, drives the motor of the first moving unit so that the deviation amount is within the predetermined possible range if the obtained deviation amount is outside the predetermined possible range, and performs the alignment of the examination unit with respect to the eye by driving the motor of the second moving unit when the deviation amount is within the predetermined possible range.

2. The ophthalmic apparatus according to claim 1, further comprising an informing unit which informs that the chin rest is to be moved by the first moving unit.

3. The ophthalmic apparatus according to claim 1, further comprising:

a mode-selecting switch for selecting any one of a first examination mode in which the examinee him/herself performs examination and a second examination mode in which the examiner performs the examination; and a sensor for sensing that the chin of the examinee is placed on the chin rest, wherein a detection signal from the sensor becomes a trigger for starting alignment in a case where the first examination mode is selected.

4. An ophthalmic apparatus comprising:

a base;

a face supporting unit which is fixed to the base;

a chin rest being movable up/down with respect to the face supporting unit, on which a chin of an examinee is placed;

a first moving unit having a motor, which puts the chin rest into up/down movement;

an examination unit being movable up/down with respect to the base, which has an examination optical system for examining an eye of the examinee;

a second moving unit having a motor, which performs alignment of the examination unit with respect to the eye of the examinee fixed to the face supporting unit by putting the examination unit into up/down movement;

an image pickup unit which picks up an image of the eye of the examinee fixed to the face supporting unit;

a movement limit detection unit which detects a movement limit of the up/down movement of the examination unit by the second moving unit; and a control unit which obtains a position of the eye in an up/down direction based on the image picked up by the image pickup unit when the movement limit is detected by the movement limit detection unit during the alignment by the second moving unit, drives the motor of the first moving unit so that the obtained position is within a predetermined possible range of the alignment in the up/down direction, which is narrower than a possible range of the up/down movement of the examination unit by the second moving unit, and performs the alignment of the examination unit with respect to the eye by driving the motor of the second moving unit when the position is within the predetermined possible range.

* * * * *